United States Patent [19]
Beyer et al.

[11] 3,960,003
[45] June 1, 1976

[54] AUTOMATIC SYSTEM FOR HIGH PRESSURE LIQUID CHROMATOGRAPHY

[75] Inventors: William F. Beyer, Portage Township, Kalamazoo County; David D. Gleason, Oshtemo Township, Kalamazoo County, both of Mich.

[73] Assignee: The Upjohn Company, Kalamazoo, Mich.

[22] Filed: Nov. 11, 1974

[21] Appl. No.: 522,455

[52] U.S. Cl. .............................................. 73/61.1 C
[51] Int. Cl.² .......................................... G01N 31/08
[58] Field of Search .................... 73/61.1 C, 423 A

[56] References Cited
UNITED STATES PATENTS

| | | | |
|---|---|---|---|
| 3,469,438 | 9/1969 | Gaumer | 73/423 A X |
| 3,530,721 | 9/1970 | Hrdina | 73/423 A |
| 3,546,946 | 12/1970 | Smith | 73/423 A |
| 3,604,269 | 9/1971 | Smith et al. | 73/423 A X |
| 3,754,443 | 8/1973 | Harris, Sr. et al. | 73/423 A X |
| 3,842,679 | 10/1974 | Iwao et al. | 73/423 A |

*Primary Examiner*—Richard C. Queisser
*Assistant Examiner*—Joseph W. Roskos
*Attorney, Agent, or Firm*—Woodhams, Blanchard and Flynn

[57] ABSTRACT

An apparatus and process for automatic high pressure liquid chromatography utilizing an automatic liquid sampler, a sample transport device, a high pressure sampling valve, a liquid chromatograph having a detector, a recorder and an integrator. Timing devices associated with the foregoing components automatically control and synchronize the chromatographic events, such as the volume and duration of the sampling and rinse functions, the mobile phase pump refill, and sample injection and the overall chromatographic cycle time. This apparatus has a last sample stop capability, and one embodiment can produce forty 20 minute chromatograms in approximately thirteen hours of unattended operation.

13 Claims, 6 Drawing Figures

AUTOMATIC SYSTEM FOR HIGH PRESSURE LIQUID CHROMATOGRAPHY

BACKGROUND OF THE INVENTION

This invention relates in general to high pressure liquid chromatography and, more particularly, to an apparatus and process for conducting such chromatography automatically with respect to a plurality of liquid test samples during an extended period of time without the attention of an operator.

Persons familiar with the use and operation of liquid chromatographs have been aware of the need for complete automation thereof. Presently, the injection of test samples is carried out manually by an operator who must be present almost constantly because he must manually inject a new test sample into the chromatograph after the recording of the preceding test sample has been completed. Often the cycle time of each sample is as small as 10 minutes so that it is difficult for the operator to perform any other beneficial duties without compromising the efficient operation of the chromatograph. This arrangement is not only boring for the operator, but also wastes valuable human resources represented by the skill of such an operator.

In the great majority of existing liquid chromatographs, the sample liquid is manually injected into the chromatograph through a septum so that the performance of the chromatograph is dependent to a considerable extent upon the technical skill of the operator who performs the injections. An improper injection can produce an unreliable run or assay which must then be thrown out. While some attempts have been made to overcome the inaccuracies produced by manual injections, as by using a valved injection mechanism, this operation has still required the presence of an operator to actuate the valve at the proper time for each test sample.

Refilling of the liquid phase pump for the chromatograph has heretofore been on demand, namely, when a sensor indicated the pump needed refilling. Often, the filing function occurred during the movement of a test sample through the chromatograph. It has been found that such an occurrence can adversely affect the accuracy of the chromatogram for that test sample.

In the past, liquid chromatographs have not always had a completely foolproof and reliable rinsing function. Thus, the assay from one sample has sometimes been made inaccurate by a carry-over of a preceding test sample.

With existing apparatus for performing high pressure liquid chromatography, it is often necessary to introduce into each test sample a standard having a sufficiently different molecular structure than the material being analyzed that a comparison can be made to determine the concentration of the test material present. However, by using the equipment to be described hereinafter, it is believed that the need for such a standard can be materially reduced because of the greater accuracy procedurewise and timewise with which the injection of the test sample can be effected, and because the virtual elimination of the human error.

Accordingly, a primary object of this invention is the provision of an apparatus including a high pressure liquid chromatograph, for automatically and successively analyzing and recording the ingredients in a plurality of test samples over an extended period of time without the attention of an operator.

A further object of this invention is the provision of an apparatus, as aforesaid, in which a small portion of any given liquid test sample is separated from the remainder of that test sample and injected into the chromatograph at a preselected point in time with reference to the completion of the analysis of the next preceding test sample.

A further object of this invention is the provision of an apparatus, as aforesaid, including a rinse and sample transport system for automatically, and at a preselected point in time with reference to the cycle of analyzing the next preceding test sample, purging the transport system with said rinse and thereafter delivering said other sample to said chromatograph.

Other objects and purposes will become apparent to persons familiar with this type of equipment upon reading the following specification and examining the accompanying drawings, in which.

Figure 1:
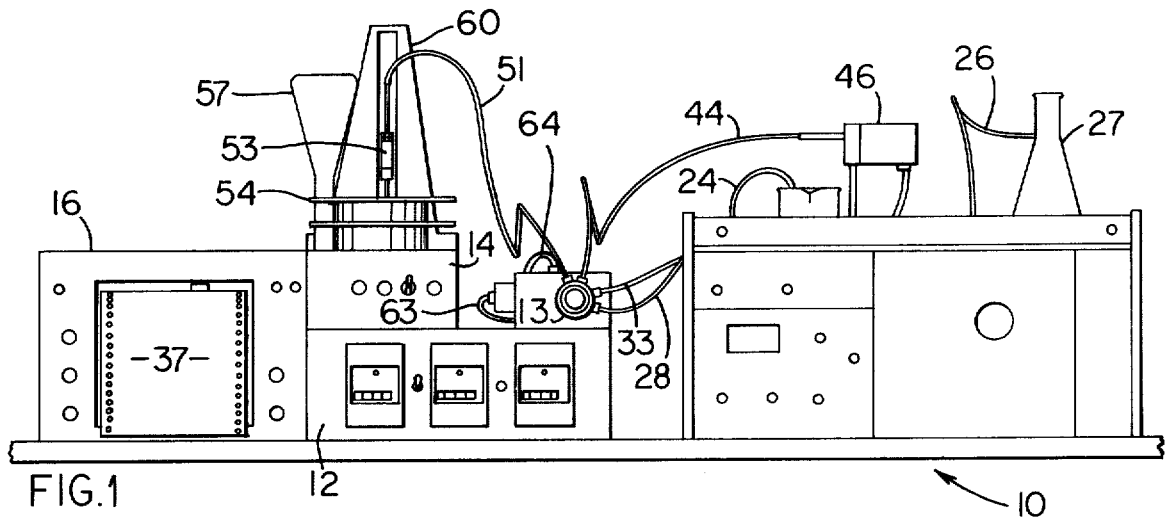
FIG. 1 is a side elevational view of an apparatus for carrying out automatic high pressure liquid chromatography.

For convenience in description, the terms "upper", "lower", "left", "right", "front" and "rear" will have reference to the apparatus of the invention and parts thereof as appearing in FIG. 1, which shows the front of the apparatus. The terms "inner" "outer" and derivatives thereof will have reference to the geometric center of the individual components of which said apparatus is comprised.

SUMMARY OF THE INVENTION

The objects and purposes of the invention, including those set forth above, have been met by providing apparatus comprising a high pressure liquid chromatograph, which is connected by suitable liquid transport means to a source of mobile phase and to a recorder and/or other suitable monitoring means. The flow of mobile phase is controlled by a valve which is also connected to a source of test samples and a rinse liquid. Timers and appropriate circuitry control the operation of the apparatus so that a small portion of a given test sample is injected into the mobile phase and thereafter passed through the chromatograph where its contents are analyzed and thereafter recorded. The test sample line is rinsed after each injection of a test sample.

DETAILED DESCRIPTION

Figure 2:
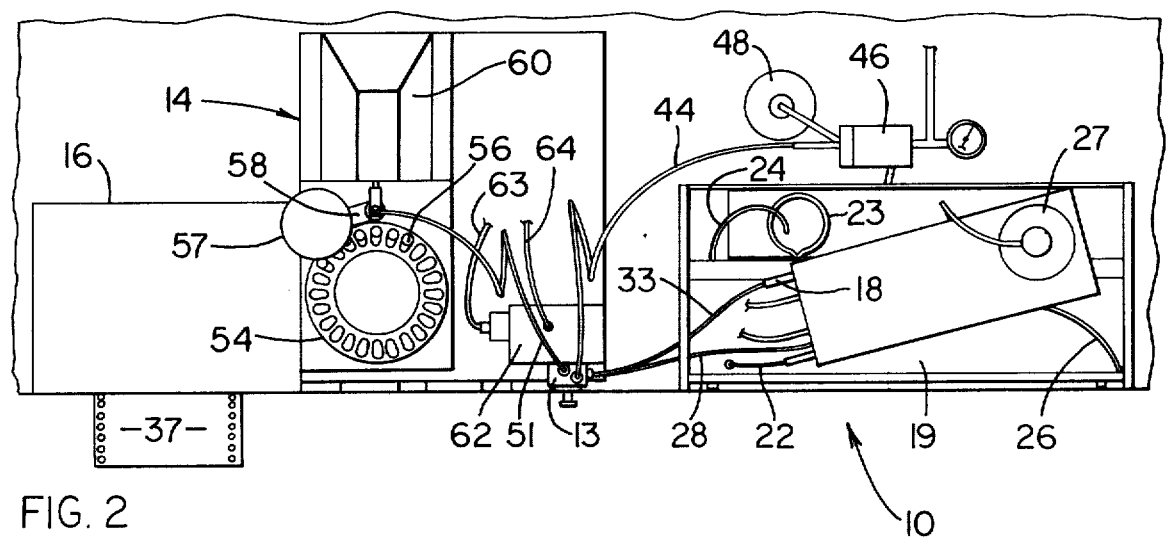
FIG. 2 is a top view of said apparatus.

The apparatus 10, FIGS. 1 and 2, is comprised of a high pressure liquid chromatograph 11, s timing control 12, a high pressure sampling valve 13, an automatic sampler 14 and a recorder 16, which may be provided with an integrater.

Figure 3:
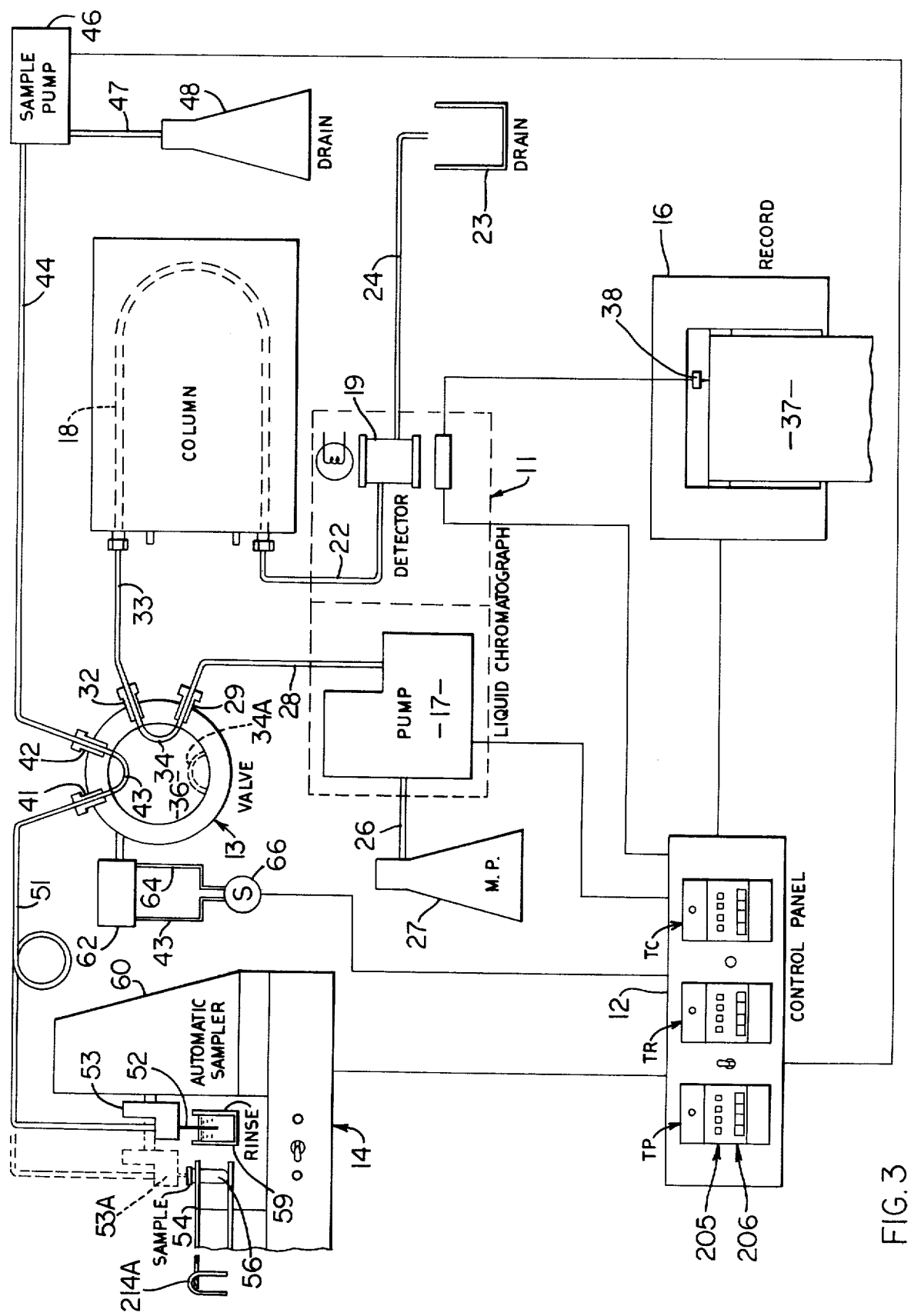
FIG. 3 is a schematic diagram of the aforesaid apparatus.

The chromatograph 11 may be of the type manufactured by Waters Associates, Inc. of Milford, Mass. and identified by Catalog No. 98208, said chromatograph being also designated as Model ALC-202 with ultraviolet detector and 6000 psi pumping system. More specifically, as shown in FIG. 3, the chromatograph 11 includes a pump 17, a packed column 18 and a detector 19, the inlet of which is connected to the outlet end of the column 18 by a line 22. The outlet of the detector 19 is connected to a drain 23 by line 24. The detector 19, which may be an ultraviolet spectrophotometer or of other desired type, produces a signal which is transmitted to the recorder.

The pump 17 may be a constant volume pump of the type made by the Milton Roy Company of St. Petersburg, Fla. and identified as a "miniPump".

The inlet of the pump 17 is connected by line 26 to a supply of carrier liquid or mobile phase 27. The outlet of the pump 17 is connected by line 28 to one inlet port 29 on the valve 13. An outlet port 32 on the valve 13 is connected by line 33 to the inlet end of the column 18. A passageway 34 in the valve core 36 normally connects the inlet port 29 with the outlet port 32. The recorder 16 may be of any convenient type, such as that manufactured by Honeywell located at Philadelphia, Pa. and identified as "electronik 19".

Said recorder 16 is equipped with a supply of graph paper 37 engaged by an inked stylus 38 in a conventional manner, and with an integrator made by Disc located at Santa Ana, Calif. and identified as "Disc" integrator.

The sample valve 13 may be a high pressure sample valve of the type manufactured by Glenco Scientific, Inc. of Houston, Tex., and identified by Catalog No. SVOV-4-1X, capable of handling up to 3000 psi and equipped with an air actuator. Said valve 13 has an inlet port 41 and an outlet port 42 which are connected by passageway 43 in the core 36. The outlet port 42 is here connected by line 44 to a source of vacuum, such as the sample pump 46, the positive pressure side of said pump being connected by line 47 to drain 48.

The inlet port 41 of valve 13 is connected by line 51 to the probe 52 mounted upon the probe carriage 53. The sampler 14 and its carriage 53 may be substantially as disclosed in the Smith Pat. No. 3,546,946, issued Dec. 15, 1970. More specifically, the sampler 14 includes a circular rack 54 (FIG. 2) mounted for rotation around a vertical axis and capable of supporting a plurality of test sample containers 56 which can be moved, one at a time, by rotation of the rack 54 into and, later, out of a position directly below the probe carriage, as shown in broken lines at 53A in FIG. 3.

A supply of rinse liquid 57, FIG. 2, is mounted on the automatic sampler 14 and is connected by tube 58 to a rinse liquid receptacle 59, FIG. 3, supported below the solid line position of the probe carriage 53. The carriage 53 moves the probe 52 upwardly out of the rinse receptable 59, outwardly and then downwardly into a sample container. At a specified time, the probe 52 is moved upwardly, inwardly and downwardly into the receptable 59. During this cycle, a sample is moved through lines 51, 44 and into passageway 43. After the valve 13 has been operated, as discussed hereinafter, the lines 51, 44 and passageway 43 are purged with rinse liquid.

The valve core 36 is rotated by the air actuator 62 between the position thereof shown in FIG. 3, with the passageways 34 and 43 in solid lines, and a position wherein passageway 43 is located in the position of passageway 34 and passageway 34 has moved down into the broken line position of 34A. This operation, which is of relatively short duration, permits the movement of a portion of the test sample into line 33.

The lines 63 and 64 are connected to the opposite ends of the actuator 62 and through the solenoid valve 66 to a source (not shown) of compressed air.

The rack 54 on the automatic sampler 14 is provided with appropriate switch actuating means, described hereinafter in connection with the circuitry of FIGS. 4 and 5, whereby substantial portions of the apparatus 10 are de-energized when the last test sample reaches the position shown in FIG. 3.

The automatic sampler 14, the solenoid valve 66, the pump 17, the detector 19, the recorder 16 and the sample pump 46 are all electrically connected to and controlled by the timing control 12, whereby the operations thereof are effected and synchronized.

While particular examples of manufactured components have been mentioned above, it will be understood that the present invention is not limited thereto and that other components may be substituted. For example, the discussed chromatograph 11 may be replaced with one made by E. I. DuPont, DeNemours and Co., Inc., Instruments Products Division, located at Wilmington, Del. under Model No. 820LC. Similarly, a variety of detectors of any desired type, not necessarily ultraviolet, may be utilized depending on the particular characteristics of the testing to be performed. The sample valve 13 alternatively may be a linear, rather than rotary, unit such as made by Hamilton, located at Whittier, Calif. designated 5000 psi High Pressure Sampline Valve and modified for automatic operation of its manual injection button by a spring returned air cylinder. Also, a DuPont high pressure sample valve may be used.

Also, a Technicon Sampler made by Technicon, Incorporated of Tarrytown, N.Y. under Model No. II may be used.

Further a refillable constant pressure pump may be substituted for the Milton Roy constant volume mobile phase pump. A known constant pressure pump is available from Haskel of Burbank, Calif. under Model No. 26740. Such pump has about a 70 milliliter capacity and provides a fixed maximum volume output at a constant pressure whereafter it must be refilled, and indeed preferably is refilled with mobile phase before each injection through the sampling valve 13 and into the chromatographic column. The Milton Roy constant volume pump, on the other hand, requires no periodic refilling. The circuitry of FIG. 4 makes provision for either type mobile phase pump.

Instead of a vacuum or suction sample pump located at 46, liquid moving means may be placed as desired between probe 52 and drain 48. Alternately, the sample and rinse containers may be suitably seal-connectible to probe 52 and to a pressurized gas source for pressure urging sample and rinse liquids from their containers through the sample valve 13.

Figure 4:
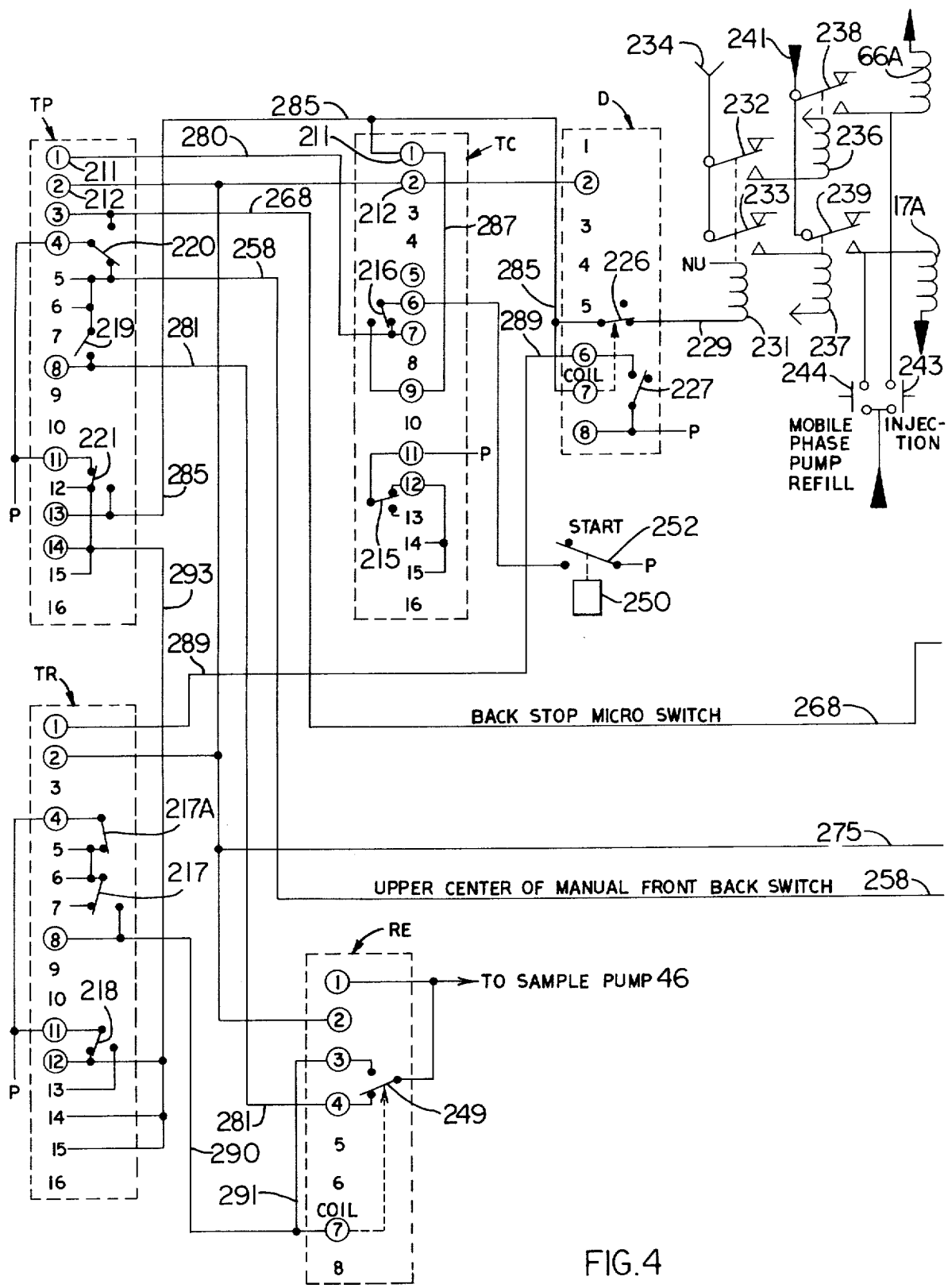
FIG. 4 is a schematic of the electrical circuitry utilized in said apparatus.

FIG. 4 discloses electrical circuitry of, and associated with, timing control 12. Thus, timing control 12 includes a pump timer TP, a rinse timer TR and a chromatograph timer TC, a time delay relay D, an injection control relay system JC and a relay RE.

Faces of the timers TP, TR and TC (FIG. 3) are exposed on the control panel of the timer control 12, and each include a preferably digital readout 205 of the unexpired portion of the interval timed thereby. The timer faces also each include a manually actuable input, preferably of push button type, for setting the interval to be timed.

The FIG. 4 circuit, with exceptions hereafter noted, is preferably powered by a 115 volt AC supply, having a "hot" side P and a "neutral" side NU. Each timer TC, TR and TP (FIG. 4) includes a terminal 211 responsive to a voltage signal from a voltage supply terminal P to start timing. Each timer TC, TR and TP also includes a further terminal 212 responsive to connection to the return (neutral) side NU of the voltage supply to enable timing initiation by such energization of timer start terminal 211.

Each timer further includes actuable contacts, or switches, which are shown in FIG. 4 in their normal (prior to initiation of timing) condition. Thus, chromatograph timer TC includes contacts 216, rinse timer TR includes contacts 217, 217A and 218, and pump timer TP includes contacts 219, 220 and 221. In addition, pump timer TP includes a reset pin (TP pin 14) actuable, after pump timer TP has timed out, for resetting the pump timer.

Pump timer TP is wired for momentary start with, as mentioned, an external reset. Rinse timer TR is wired for sustained start (continuation of a starting voltage on start terminal 211 thereof does not affect normal timing of a preselected interval, as long as the continued starting signal is removed before the end of such interval). Chromatograph timer TC is wired for momentary start and automatically resets at the end of its timed interval. The timers TP, TR and TC may be ATC timers manufactured by Automatic Timing Controls, Inc. located at King of Prussia, Pa. and identified as Model 325, though other suitable timers are contemplated.

Time delay relay D may be of any conventional type capable of adjustment to time a delay in the range at least 3 to 30 seconds, being typically set for about a 4 second time delay. Delay relay D includes contacts 226 and 227. Contact 227 is normally open but closes after delay timing by delay relay D. Contact 226 is normally closed but opened after time delay. The relay RE includes a double throw contact 249.

Injection control relay system JC actuates the coil 66A of solenoid valve 66 (FIG. 3) controlling the actuator 62 for sampling valve 13. In addition, relay system JC actuates, where the mobile phase pump 17 is of the refillable type, a plunger return solenoid 17A of such refillable pump. Where a non-refillable pump, e.g. a continuously operated constant volume mobile phase pump is employed, the refill solenoid 17A is not present and the remaining circuit elements for mobile phase pump refill, hereinafter described, do not act, or may be omitted.

An input signal line 229 connects relay system JC to contacts 226 of delay relay D. While it is contemplated that an appropriate voltage signal on input line 229 can be utilized directly to actuate solenoids 66A and/or 17A, the relay system JC here includes a 115 volt AC relay 231 actuable by line 229 and having normally open contacts 232 and 233 disposed between a 24 volt DC supply, indicated by the shallow V-shaped symbol 234, and 24 volt DC relay coils 236 and 237. The latter coils connect to the return side of the 24 volt DC supply and actuate respective normally open contacts 238 and 239. Contacts 238 and 239 are each closable to connect a 24 volt AC supply terminal, indicated by the arrow symbol 241, to the respective solenoid coils 66A and 17A, in turn coupled to the return side of the 24 volt AC supply. In addition, normally open switches 243 and 244 effectively parallel contacts 238 and 239, respectively, being interposed between the 24 volt AC supply and solenoid coils 66A and 17A and being manually closable for manual actuation of the respective coils, 66A and 17A.

The interposition of the 24 volt DC switches 232, 233 and relay coils 236, 237, between input line 229 and the solenoids 66A and 17A, allows optional operation of the latter by additional external means, such as a computer, if desired. The inclusion in relay system JC of the 24 volt AC switches 238 and 239 conveniently allows use of the 24 volt AC solenoids 66A and 17A normally provided with the particular rotator 64 for sampling valve 13 and particular refillable mobile phase pump used in one embodiment of the invention. Thus, the relay system JC primarily provides desirable and convenient voltage magnitude and type interfacing between input signal line 229 and the injection valve and mobile phase pump solenoids 66A and 17A, and permits manual actuation of the latter.

In addition, the timing control 12 includes a normally open manual start switch 252, momentarily closable for initiating a single cycle of apparatus operation (chromatograph run for a single sample) and which may be latched closed, by any conventional means indicated diagramatically at 250.

Figure 5:
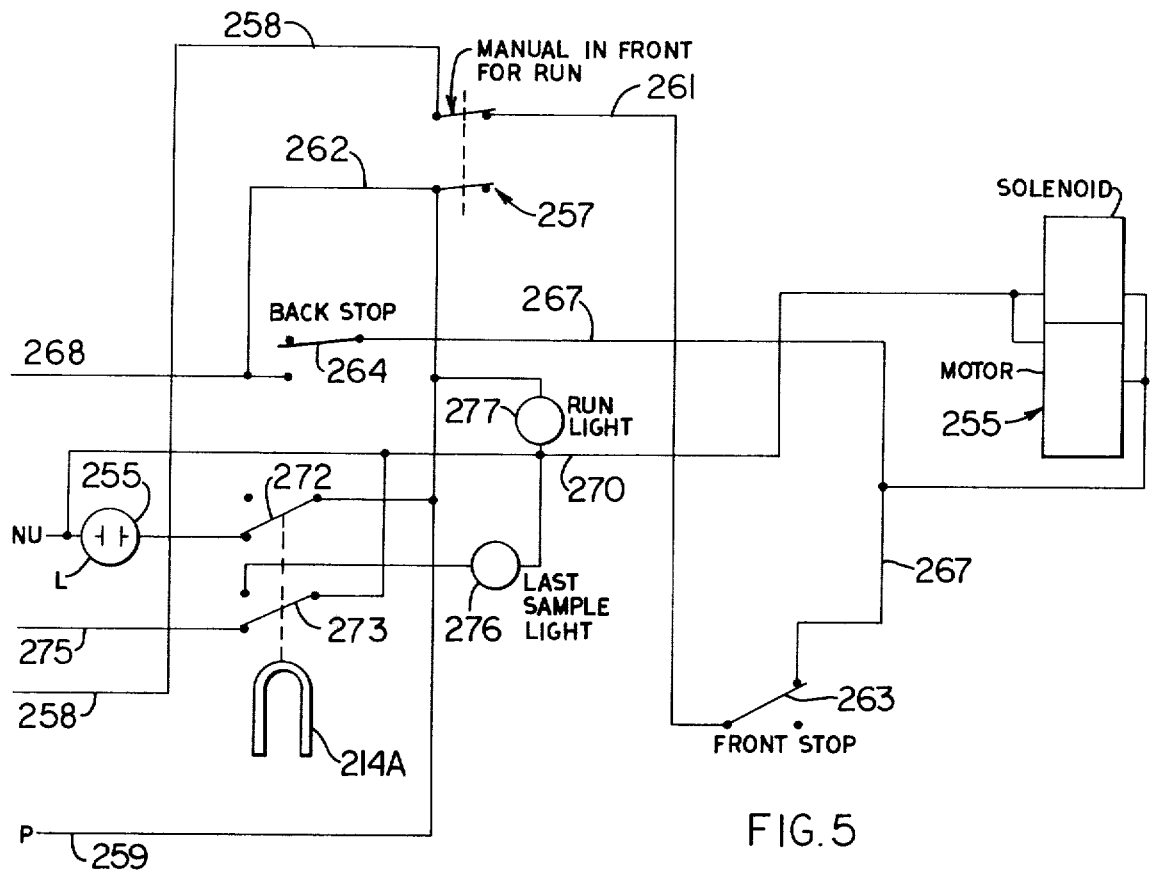
FIG. 5 is a schematic of control circuit for an automatic sampler.

FIG. 5 discloses a typical control circuit for the automatic sampler carriage 53 of FIG. 3 to replace circuitry portions in an existing automatic samplers 14. The FIG. 5 circuit is particularly adapted for use with the automatic sampler of the aforementioned Smith Pat. No. 3,546,946. The motor 255 (FIG. 5) is that normally provided for forward and rearward shifting of sampler carriage 53 (FIG. 3) to its sample and rinse positions. The present invention in FIG. 5 provides a manually actuable double pole-double throw front-back switch 257 for manual shifting of the carriage 53 between front and rear positions. For automatic operation the switch 257 is manually positioned in its rightward, front position shown. The upper and lower center terminals of switch 257 respectively connect through lines 258 and 259 to the contact 220 in pump timer TP (FIG. 4) and to the 115 volt AC supply terminal P. The upper right and lower left selectable terminals of switch 257 connect through respective lines 261 and 262 to a front stop switch 263 and a rear stop switch 264, such switch being connected in parrallel to one side of the motor 255 through respective lines 266 and 267. Additionally, the back stop switch 264 connects through line 268 to pump timer TP pin 3, which is alternately selectable by pump timer contact 220. The switches 263 and 264 correspond to the conventional front and rear limit switches of the Smith Patent automatic sampler and are similarly opened by movement of the sampler carriage 53 into its front and rear positions respectively. The remaining side of carriage motor 255 connects through a line 270 to the neutral side NU of the 115 volt AC supply.

An additional double pole double throw switch includes an automatic shut down contact 272 and a timer reset contact 273 actuable means on the sample rotor 54. The latter may be a fixed lug on the sampler carriage in a Smith type sampler or may be provided as a moveable U-shaped member as at 214 A in FIG. 3 on another sampler. Thus, when the last sample container 56 of a series sample rotor 54 moves into sampling position (which last sample is conveniently a dummy sample) the resulting upward actuation of contacts 272 and 273 shut down the apparatus.

Contact 272 is normally closed to connect the 115 volt AC potential line 259 through a conventional electrical receptacle 255 to the AC supply neutral side NU. The major components of the apparatus, including the sampler 14, recorder 16, the FIG. 4 circuitry connections to the hot side P of the AC supply, etc. normally receive operating potential from the AC supply through receptacle 255 so that opening of contact 272 effectively shuts down all major components of the apparatus. An exception may be the ultraviolet lamp associated with an ultraviolet detector 19, since substantial warm-up time, such as half a day, is normally required for correct operation of such a detector lamp.

The timer reset contact 273 normally connects from AC supply neutral side NU through reset line 275 to the pin 2 of each of the three timers and two relays in the FIG. 4 circuit (in 212 of the timers) to permit their operation. Upward actuation of contact of 273 breaks this connection to neutral, resetting the FIG. 4 timers and relays, and ignites a last sample lamp 276 to indicate that the last sample has been processed. If desired, a run lamp 277 may be connected across the AC supply to indicate connection of the FIG. 5 circuitry thereto.

The interconnection of the above mentioned FIG. 4 and FIG. 5 circuit elements is more fully discussed in the following description of operation.

OPERATION

Referring to FIGS. 4 and 5, the various contacts are normally positioned as shown. Operating potential on the hot supply terminals P is applied through contact 220 of pump timer TP (at TP pin 4) and thereby through line 258, manual front-back switch 257 (FIG. 5), line 261, and front stop switch 263 to the sampler carriage motor 255. The latter shifts the sampler carriage 53 to its front position, engaging the probe with a sample container 56.

The stop switches 263 and 264 are limit switches conventionally opened by a forward and rearward placement, respectively, of the carriage 53. Thus, rear stop switch 264 closes and front stop switch 263 now opens, shutting off carriage motor 255 in the forward carriage position.

Apparatus operation may then be initiated by manual closure of start switch 252, either momentary or sustained by latch 250. Start switch closure applies operating potential from supply terminal P (here 115 volts AC) through a line to contacts 216 (coupling TC pins 6 and 7) of chromatograph timer TC and a line 280 to the start terminal 211 of pump timer TP. Pump timer TP then starts timing the sample pump interval (e.g. 2 minutes) indicated in FIG. 6. Such energization of pump timer start terminal 211 shifts instantaneous contact 219 (to TP pin 8) to apply potential from supply P (at TP pin 4) through serial contacts 219 and 200 and a line 281 to contact 249 of relay RE (at RE pin 4). Such relay contact 249 applies the potential through a line 283 to actuate the sample pump 46 (FIG. 3).

As stated, prior to the sample pump time, forward (sample engaging) placement of the sample carriage 53 has been insured. When actuated, sample pump 46 draws sample liquid through the line 51, the sample ports 41 and 42 of the sample valve 13, and line 44 toward the drain 48. The sample pump interval is sufficient to ensure filling of the sample valve passageway 43 with sample liquid.

Timing out of the sample pump timer TP ends the sample pump interval and shifts its delayed contacts 220 and 221 from their positions shown in FIG. 4.

Such shifting of contact 220 removes operating potential from line 258 and thus from open front stop switch 263 (FIG. 5). Shifting contact 220 also removes potential from contact 219 and line 281, shutting off the sample pump 46.

The thus shifted contact 220 (to TP pin 3) applies potential from supply P through line 268, back stop switch 264 (FIG. 5), and line 267 to sampler carriage motor 255. The latter returns the carriage 53 to its rear position to immerse probe 52 in rinse receptacle 59 and to restore stop switches 263 and 264 to their positions shown. The sample pump deenergization occurs before the probe 52 has left the sample liquid, preventing an air bubble in the probe and communicating lines 41, 43 and 44 and thereby preventing the disturbance such an air bubble would make in the operation of the column 18 and detector 19.

The aforementioned shifting of contact 221 (to TP pin 13) applies operating potential from supply P through a line 285 to start terminal 211 of chromatograph timer TC and to the coil (D pin 7) of delay relay D. Thus, the chromatograph timer and delay relay begin timing, respectively, the chromatograph interval (FIG. 6) which may last any desired time, for example 20 minutes, and the delay interval (FIG. 6) which may last, for example 4 seconds. Simultaneously with initiation of these intervals, the operating potential on line 285 is applied through normally closed contact 226 of delay relay D and line 229 to the AC relay coil 231 of the injection relay system JC.

With the actuation of injection relay system JC, the various contacts are closed in the manner above discussed to energize solenoid 66 A of sampling valve rotation solenoid 66 (FIG. 3), rotating the sample containing passageway 43 thereof into communication with ports 32 and 29 and hence with the mobile phase pump 17 and column input conduit 33. If a refillable mobile phase pump 17 is utilized, its refill solenoid 17 A is similarly actuated to cause rapid refilling of the pump to full capacity and initiation of its output stroke of mobile phase liquid through line 228 so as to carry the sample in passageway 43 into the column 18. Solenoid 17 A is not used with a mobile phase pump of the continuous run, constant volume type. In this instance, the output of the mobile phase pump 17 is directed through line 28 and sample containing passage 43 to similarly flush the sample liquid into the column 18. During this time, the passageway 34 of valve 13 has been in its down or broken line position 34 A. The above steps, accomplished by actuation of relay system JC, occur during the delay interval. The delay interval also affords time for the aforementioned shifting of the probe carriage from its forward to its rearward position.

Returning to the initiation of the chromatograph interval, the potential applied by line 285 to chromatograph timer start terminal 211 immediately shifts instantaneous contact 216 from its position shown, connecting start switch 252 there through to line 287 back to the start terminal 211 of the chromatograph timer. Where the start switch 252 is held closed for a continuous run, the result will be application of operating potential from supply P through switched contact 216 and line 287 (through TC pins 6 and 9) to maintain energization of the chromatograph timer start terminal 211.

This lock-in effect on the chromatograph timer start terminal is of course not present if the start switch 252 was allowed to open after initiating a cycle of apparatus operation (i.e. for a single cycle operation).

The delay time, or time for injection of the sample into the column 18, ends with timing out of delay relay D. Timing out of delay relay D opens its contacts 226 and closes its contact 227.

Opening contact 226 deenergizes injection relay system JC by removing the operating potential previously applied thereto along lines 285 and 229. This deenergizes solenoid coil 66 A, for returning solenoid 66 and causing valve rotator 62 to rotatably return valve 13. Valve passageway 43 thus returns to series connection with liquid lines 51 and 44, and valve passage 34 returns to communication with mobile phase pump 17 and column 18, as shown in FIG. 3. The mobile phase pump 17, be it of refillable or constant run type, continues to supply mobile phase to line 28, passageway 34 and line 33 to column 18, thereby gradually moving the slug previously injected of sample liquid along the column 18 at the desired rate for component separation therein and application to the detector 19.

Figure 6:
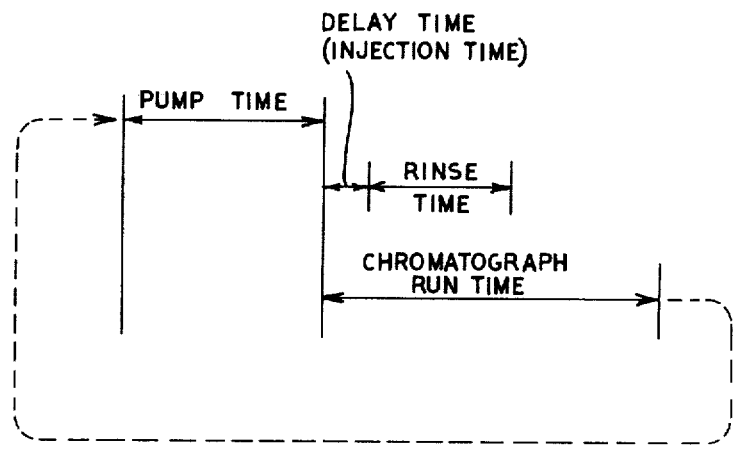
FIG. 6 is a timing diagram showing the interrelation between timing periods provided by the circuitry of FIG. 4.

Such closing of delay relay contact 227 couples (through D pins 8 and 6) operating potential from supply P through a line 289 to start terminal 211 of rinse timer TR, starting the latter to initiate timing of the rinse interval (FIG. 6). The Contact 217A of rinse timer TR is permanently closed and series instantaneous contact 217 of rinse timer TR immediately closes (coupling TR pins 4 and 8) and thereby apply operating potential from supply P through a line 219 to the coil of relay RE and also applying operating potential to further line 291. The thus energized relay coil shifts contact 249 upward (to RE pin 3) and from the operating potential on line 291 thus again energizes sample pump 46. The sample pump 46 then moves rinse liquid from rinse receptacle 59 through probe 52, line 51, passage 34 and line 44 to drain 48 for the remainder of the rinse interval and thereby removes all traces of the last supplied sample from this path.

Also, the mentioned upward shift of relay RE contact 249 breaks its connection to line 281 to isolate the sample pump 46 from the pump timer TP for the remainder of the cycle of operation.

The rinse timer, TR times out after a preselected interval (e.g. 5 minutes). Prior to timing out, rinse timer TR contact 218 had applied operating potential from supply P through a line 293 to pump timer TP (at TP pin 14) preventing resetting of such pump timer. However, timing out of rinse timer TR opens contact 218 thereof, removing operating potential from such line 293 and causing pump timer TP to reset, returning its contact 219-221 to their initial positions shown. Such opening of rinse timer contact 218 also (by removing operating potential from TR pin 12) resets the rinse timer, returning its contact 217 to the initial open position. This removes potential from lines 290 and 291, deenergizing the sample pump 46 and the coil relay RE. Thus rinse flow from probe 52 through sampling valve passageway 43 ceases at the end of the rinse interval.

On the other hand, the simultaneous resetting of the pump timer TP contacts 219, 220 and 221 ensures first that no potential will be applied by line 281 through relay RE to the sample pump 46, second that operating potential is removed from line 285 to chromatograph timer start terminal 211, the coil of the delay relay D and the contact 226 of the latter and the third that operating potential is once again applied (by contact 220) to line 258.

The operating potential applied by reset pump timer contact 220 to line 258 is, as before the start of the above described cycle, applied through manual switch 257 (FIG. 5), line 261 and the closed front stop switch 263 to sampler motor 255 which again shifts the automatic sampler carriage 53 forwardly. The probe 52 leaves the rinse liquid after the sample pump 46 is deenergized, thus preventing an air bubble in line 51, and goes into a new sample container 56. The new sample 56 was placed in a carriage path by conventional internal rotor control circuitry of sampler 14 (not shown) while sample carriage 53 was in or entering its rearward, rinse position above described. The present forward shifting of sampler carriage 53 again closes back stop switch 264 and opens front stop switch 263 shutting off carriage motor 255 as the carriage 53 reaches its front, sampling position.

Eventually, chromatograph timer TC times out, ending the chromatograph interval (FIG. 6). Thereupon, delayed contact 215 (by removing operating potential from TC pin 12) resets chromatograph timer TC restoring its contact 216 to the position shown in FIG. 4. The latter removes the connection from start switch 252 through line 287 (and TC pin 9) to chromatograph timer start terminal 211, preventing any false start of the latter, and reestablishes the connection from start switch 252 through line 280 to start terminal 211 of pump timmer TP. This ends one cycle of apparatus operation.

If the start switch 252 is open at this time a second cycle of apparatus operation will not occur until start switch 252 is again manually closed. On the other hand, if start switch 252 was still held closed at this time (as by latch 250) the apparatus will automatically begin a second cycle of operation. In either case, a second cycle proceeds in the manner described above with respect to the first. All three timers and both relays of FIG. 4 have been reset, in the manner above discussed, by the end of the chromatograph interval and are thus in condition for starting a new operation cycle. The total cycle time is the sum of the pump and chromatograph intervals, as seen in FIG. 6.

In the automatic mode (start switch 252 held closed), cycling of the apparatus continues until the ganged auto stop and timer reset contacts 272 and 273 are actuated upward by the above described last sample lug or member on the rotating sample rack 54. The thus shifted timer reset contact 273 opens the line 275, thereby removing the neutral connection to pins 2 of the FIG. 4 timers and relays, preventing their further operation and resetting same, where not already reset, for future use. Timer reset contact 273 simultaneously activates last sample lamp 276 to indicate the condition of the apparatus.

Opened auto stop contact 272 breaks line 259, disconnecting power receptacle L from the 115 volt AC supply. Preferably all portions of the apparatus shown in FIGS. 3 and 4 receive their 115 volt AC potential from receptacle L (except the ultraviolet lamp of an ultraviolet type detector 19, where such is used) which effectively shuts down the apparatus until contacts 272 and 273 are restored to their positions shown by manual intervention. The contacts 272 and 273 are preferably also manually operable to enable manual stopping of the apparatus at any time by an upward shift of either or both of contacts 272 and 273 (or their parallel counterparts not shown).

If desired, the system may be controlled, e.g. by a momentary type actuation of the start switch 252 to enable an initial "test" sample to be processed through a cycle or portions of a cycle (using manual actuation of contact 273 to stop in mid-cycle). This preliminary run allows selection of optimum time interval settings (particularly for the chromatograph interval), whereafter a series of samples can be run automatically by the apparatus without need for human attendance.

Although a particular preferred embodiment of the invention has been disclosed in detail for illustrative purposes, it will be recognized that variations or modifications of the disclosed apparatus, including the rearrangement of parts, lie within the scope of the present invention.

The embodiments of the invention in which an exclusive property or privilege is claimed are defined as follows:

1. An apparatus for carrying out automatic high pressure liquid chromatography on a plurality of test samples, one after the other, comprising:
   a source of test samples and a source of rinse liquid and means for selectively connecting said sources to a first flow path;
   means associated with said first flow path for moving said test samples and rinse liquid alternatively therealong;
   a high pressure liquid chromatograph and means associated therewith for producing chromatograph test results;
   a source of liquid mobile phase and a second flow path isolated from said first path and extending from said liquid mobile phase source to the chromatograph;
   a movable valve core containing a double ended fixed volume passage and means which in a load position of said valve core connect said core passage in series within said first path for filling by sample liquid moving along said first path;
   means for (1) shifting the filled fixed volume core passage entirely out of communication with said first path while closing both valve-connected ends of said first path and for (2) instead interposing said filled core passage serially in said second path such that mobile phase flow advances to said chromatograph only the fixed quantity of sample liquid stored in said core;
   timing control means for synchronizing and actuating said selectively connecting means, said means for moving and said means for shifting and interposing.

2. The apparatus of claim 1, in which said movable valve core includes a second double ended passage isolated from said first mentioned passage and located in the valve core for interposition in said second path while said first mentioned passage is interposed in said first path, said first and second paths each having a maximum of one valve core passage interposable therein at any given time.

3. An apparatus for carrying out automatic high pressure liquid chromatography on a plurality of test samples, one after the other, comprising:
   a first flow path connectible to a test sample and sample delivery means associated with said path for moving liquid therethrough;
   liquid chromatograph means and a mobile phase delivery means for flowing liquid mobile phase to said chromatograph means through a second path;
   detector means connected to said chromatograph means for providing test results for each sample tested;
   valve means having a passage normally interposed in said first path for receiving a quantity of sample liquid and actuable for shifting said passage into said second path for mobile phase conduction of said quantity of sample liquid to said chromatograph means;
   pump timer means actuable for timing a pump interval and therewith actuating said sample delivery means to flow test sample liquid through said passage;
   delay timer means actuable in response to timing out of said pump timer means for timing a brief delay interval sufficient for shifting of said sample filled passage into said second path and carrying of the sample quantity therein to said chromatograph means by said mobile phase flow;
   rinse timer means actuable in response to timing out of said delay timer means for timing a rinse interval wherein said passage returns from said second path to said first path while permitting continued mobile phase liquid flow through said second path into said chromatograph means;
   a source of rinse liquid connectible to said first path; said sample delivery means being responsive to timing of said rinse timer means for rinsing said first path and passage during said rinse interval;
   chromatograph timer means actuable also in response to timing out of said pump timer means for timing a chromatograph interval at least extending through said delay and rinse intervals and sufficient for completion of detection of said test sample by said tector means.

4. The apparatus of claim 3, in which said valve means comprises a movable valve core, said passage being a double ended, fixed volume passage in said valve core, said valve means including means for connecting ends of said passage in series in said first path and further means for alternatively connecting said valve passage serially in said second path while blocking the portions of said first path connected to said valve means, such that the volume of sample liquid fed through said second path to said chromatograph means is precisely determined by the fixed volume of said passage in said valve core, said first and second paths being continually isolated from each other.

5. The apparatus of claim 3, including means responsive to timing out of said pump timer means for deactuating said sample delivery means, valve circuit means also responsive to timing out of said pump timer means for carrying out said shifting of said passage from said first path to interposed relation in said second path, and sampler means also being actuable in response to timing out of said pump timer means for connecting said rinse liquid source to said first path in place of said test sample source and completing said connection during said delay interval.

6. The apparatus of claim 5, including means responsive to timing out of said delay timer means for deactuating said valve circuit means, and means connected to said valve means for continuously urging said passage toward its position of interposition in said first path, so as to return said passage to said first path upon deactuation of said valve circuit means.

7. The apparatus of claim 6, including means responsive to actuation of said rinse timer means for re-energizing said delivery means to carry out said rinsing of said passage during said rinse interval, means responsive to said timing out of said rinse timer means for shutting off said delivery means at the end of said rinse interval, and means responsive to timing out of said rinse timer means for resetting said pump timer means to enable a future reactuation thereof.

8. The apparatus of claim 7, including means responsive to said resetting of said pump timer means for changing the connection of said first path from said rinse source to another test sample, and means actuable in response to timing out of said chromatograph timer means for resetting said chromatograph timer means for a future actuation, said rinse timer means including means for resetting itself when it times out.

9. The apparatus of claim 5, including a start switch manually actuable to start timing of said pump timer means, latch means actuable to hold said start switch actuated for automatically starting a new cycle of operation by actuation of the pump timer means upon and in response to timing out of the chromatograph timer means, said sampler means including a movable sample support means capable of carrying a plurality of test samples and being at least indirectly responsive to timing out of said rinse timer means for shiftng a new test sample into position adjacent said first path, said first path terminating in a probe insertable by said sampler means alternatively into a rinse liquid and the opposed one of said samples, means manually positionable on said sample support means following the last test sample thereon and means responsive to location of said last sample position adjacent said probe for disconnecting operating potential from the apparatus except for said detector means, whereby to automatically terminate operation after processing of a series of samples but permitting subsequent running of a new set of samples with a delay for warming up the detector.

10. The apparatus of claim 5, in which said mobile phase delivery means comprises a refillable mobile phase pump and a source of mobile phase liquid, said valve circuit means including solenoid means actuated therewith for rapidly refilling said mobile phase pump from said mobile phase source and, within said delay interval, injecting mobile phase liquid into said second path.

11. The apparatus of claim 5, in which said pump timer means, rinse timer means, and chromatograph timer means each include a digital readout indicating the unexpired portion of the interval timed thereby and a manually actuable input for setting the interval to be timed thereby so as to permit rapid tailoring of timing in the system operational sequence to requirements of a specific test run.

12. The apparatus of claim 11, in which each said timer includes a first terminal responsive to a voltage signal from a suitable voltage supply to start timing, said timers having a common connection to the remaining side of said voltage supply, said timers further including plural switches responsive to at least the beginning or end of the interval timed thereby for shifting.

13. The apparatus of claim 3, in which said pump timer means includes first, second and third shiftable contacts, said delay timer means includes first and second shiftable contacts, said rinse timer means includes first, second and third shiftable contacts and said chromatograph timer means includes first and second shiftable contacts;

said apparatus including a source of operating potential and sampler means including carriage motor means actuable for shifting a probe termination on said first path between sample engaging and rinse engaging positions, said apparatus further including a manually actuable start switch;

carriage shift means responsive to application of operating potential to said second contact of said pump timer means for causing said carriage motor means to engage said probe termination with a said test sample;

means responsive to actuation of said start switch for applying operating potential through said second chromatograph timer means contact to said pump timer means and therewith initiating timing of said pump interval and shifting of said first pump timer means contact to apply operating potential therethrough from said second pump timer means contact to a relay drive line, said sample delivery means including a sample pump and a sample pump relay having a contact normally positioned for applying operating potential from said relay drive line to said sample pump to actuate the latter;

said second and third pump timer means contacts being delayed contacts shiftable upon timing out of said pump timer means, said second pump timer means contact being shiftable to remove operating potential from said relay drive line and shut off said sample pump and condition said sampler means for engaging said probe termination with said rinse liquid source following sample pump shut-down;

means responsive to said shifting of said third pump timer means contact for applying operating potential to said chromatograph timer means and said delay timer means to start timing thereby, said last mentioned means further applying operating potential through said first delay timer means contact to a valve means shift line, said valve means comprising a shiftable valve element containing said passage and solenoid means actuable for shifting said passage from said first path to said second path in response to application of operating potential to said valve means shift line, said second chromatograph timer means contact being responsive to initiation of timing by said chromatograph timer means for shifting and thereby breaking the connection of the start switch therethrough to said pump timer means;

said first and second delay timer means contacts being shiftable by timing out of said delay timer means, the shifted first delay timer means contact removing operating potential from said valve means shift line and de-energizing said valve solenoid for returning said valve passage to said first path, means responsive to said shifting of said second delay timer means contact for initiating timing by said rinse timer means and thereby immediately shifting said first rinse timer means contact, means responsive to said first rinse timer means contact shift for causing a shift of said sample pump relay contact and applying operating potential through said shifted pump relay contact to said sample pump for rinsing said first path and valve passage, while isolating said sample pump from said pump timer means for the remainder of a cycle of operation;
means connecting said third rinse timer means contact to said pump timer means for preventing resetting of said pump timer means prior to timing out of said rinse timer means, said third rinse timer means contact being shifted in response to timing out of said rinse timer means for carrying out said resetting of said pump timer means contacts as well as said rinse timer means and thereby resetting said sample pump relay and de-energizing said sample pump;
said sampler carriage motor means being responsive to the reset condition of said second pump timer means contact for shifting said probe termination from rinse position to sample position subsequent to sample pump de-energization;
said first chromatograph timer means contact being a delayed contact shifted by timing out of said chromatograph timer means, means supplying operating potential to said first chromatograph timer means contact for resetting said chromatograph timer means upon the last mentioned contact shift and thereby resetting said second chromatograph timer means contact to again furnish a potential path between said start switch and said pump timer means and thereby initiate a further cycle of operation if or when said start switch is in its actuated condition.

* * * * *